Figure 1:
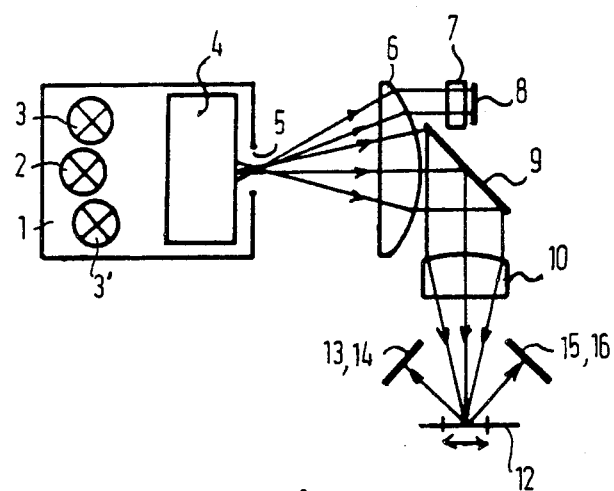

United States Patent [19]

Breemer

[11] Patent Number: 4,681,454
[45] Date of Patent: Jul. 21, 1987

[54] DEVICE FOR DETECTING DIFFERENCES IN COLOR

[75] Inventor: Johannes Breemer, Delft, Netherlands

[73] Assignee: N.V. Optische Industrie "De Oude Delft", Netherlands

[21] Appl. No.: 695,950

[22] Filed: Jan. 29, 1985

[30] Foreign Application Priority Data

Feb. 7, 1984 [NL] Netherlands .................. 8400380

[51] Int. Cl.$^4$ .................................................. G01J 3/50
[52] U.S. Cl. ...................................... 356/402; 250/205; 356/420; 356/425; 422/87
[58] Field of Search ............... 250/205; 356/402, 408, 356/420, 425, 447, 448; 422/86, 87, 90

[56] References Cited

U.S. PATENT DOCUMENTS

| | | | |
|---|---|---|---|
| 3,332,313 | 7/1967 | Batson | 356/434 |
| 3,684,378 | 8/1972 | Lord | 356/408 |
| 4,023,930 | 5/1977 | Blunck et al. | 422/87 |
| 4,181,699 | 1/1980 | Kitzinger | 422/87 |
| 4,305,659 | 12/1981 | Bilstad et al. | 356/40 |
| 4,507,556 | 3/1985 | Brenholdt | 356/338 |

FOREIGN PATENT DOCUMENTS

WO84/00211  1/1984  PCT Int'l Appl. .
1410823  10/1975  United Kingdom ............. 356/402

*Primary Examiner*—F. L. Evans
*Attorney, Agent, or Firm*—Louis E. Marn

[57] ABSTRACT

A device for detecting differences in color of a material to be inspected, which device comprises a first light source emitting light of a first color and a second light source emitting light of a second color, an optical system adapted to project portions of the light emitted both by the first and the second light source onto first and second spaced apart measuring regions respectively, each measuring region being associated with means for measuring the amount of light reflected by the material. The device further comprises electronic switching means for alternately energizing the first and the second light source, means for transporting the material, means for controlling the intensity of the second light source in dependence upon the measured amount of reflected first light source light, and means for determining a difference in color from the measured amounts of reflection.

9 Claims, 4 Drawing Figures

DEVICE FOR DETECTING DIFFERENCES IN COLOR

The invention relates to a device for detecting differences in color of a material to be inspected, which device comprises means for illuminating the material, means for measuring the amount of light reflected by the material and means for transporting the material.

The device according to the invention is particularly suited for use in a gas detection apparatus comprising a material conditioned to change in color when in contact with gases and means for establishing contact between this material and the gases. However, use of the device according to the invention is not restricted to that in a gas detection apparatus.

Such a gas detection apparatus is known from U.S. Pat. No. 4,032,297 and is designed for detecting the presence of different kinds of noxious gases in the atmosphere. In the prior art apparatus the material consists of a strip-like substrate of plastics coated with a layer of chemical substances. These substances change in color in the presence of the noxious gases to be detected and do not in the absence thereof. The presence of noxious gases is detected by illuminating a spot of measurement on the strip of material by means of a light source and measuring the light reflected from the surface of the strip of material by means of a photodiode, and by subsequently exposing the spot of measurement to the atmosphere to be monitored and repeating the measurement of the reflection after some time. An alarm signal is produced in response to the measured change in reflection exceeding a predetermined limit value. The strip of material is not transported between the measurement of the first and the second reflection value, so that one light source and one photodiode suffice.

A drawback inherent in the prior apparatus is that the discoloration of the strip of material has to be rather substantial in order to allow an accurate determination of the presence or absence of a noxious gas: in connection with intensity variations in the light source and non-linearities in, especially, the light detector and the electronic circuitry connected thereto, it is impossible to accurately determine a slight discoloration, while long term variations in the intensity of the light source and the sensitivity of the photodiode render it necessary to have the production of an alarm signal occur only in response to a rather substantial discoloration in order to prevent false alarm. However, especially when detecting extremely noxious gases, such as poisonous gases, it is of vital importance to attain a reliable indication of the presence of such gases at the earliest possible moment. For the detection of certain gases use can be made of a hydrophilic, gauzily woven, strip-like fabric, to be called ribbon for short hereinafter, which is moistened with chemical substances to exhibit no discoloration in the presence of noxious gases and to exhibit discoloration indeed in the absence of such gases. The ribbon is transported continuously. An advantage of such a ribbon is that it can be rapidly and fully impregnated with the liquid chemicals without the strength of the fabric being adversely affected. Should a more homogeneous material be used, such as a strip of paper, such impregnation would cause the material to swell up and its strength to be reduced, resulting in impaired transportation of the strip. Moreover, in the case of a paper strip the gas cannot reach the chemicals in the interior of the strip, which adversely affects the reaction rate. Besides the afore-said advantages, however, the use of ribbon moistened with chemicals entails a number of specific problems where the measurement of the color of the ribbon is concerned, while furthermore the continuous transportation of the ribbon requires, in principle, the use of two light sources and two light detectors, which places high demands on the equality of these components.

The chemical reaction producing discoloration takes some tenths of seconds to a few minutes, depending upon the activity of the reagents and the ambient temperature. However, the failure to discolor has to be established as early as possible. Experiments have shown that discoloration of the ribbon can be detected after the reaction has been allowed to take place for about 10 seconds. Not only the ultimate color of the ribbon but especially the color after a period of about 10 seconds depends highly on the prevailing temperature and the age of the chemicals. Furthermore, the color of the ribbon after 10 seconds depends on the color of the ribbon without chemicals, the manner in which the ribbon is moistened and the amount of ribbon material passing the measuring system per unit of time. Hence it is not possible to check the discoloration of the ribbon by comparing its color with some preestablished reference color. Furthermore, the ribbon is not homogeneous. The mesh width is not negligibly small in relation to the dimensions of a measuring field used in practice for color measurements, while the threads are not of uniform thickness and the spacings between the threads vary to a relatively large extent. As a result, the net thread area present within a measuring field will likewise vary. A proper operation of the gas detector therefore requires the color measurement to be optimally irresponsive to the afore-said factors.

To solve the above problems, in accordance with the invention there is provided a detection device of the above type in which the means for illuminating the strip of material include a first light source adapted to emit light of a first color and a second light source adapted to emit light of a second color, there being provided an optical system adapted to deliver essentially equal fractions of the light emitted by the first and by the second light source to first and second measuring regions spaced apart on the strip of material, each measuring region being associated with means for measuring the amount of light reflected by the strip of material, there further being provided means adapted to directly measure the amount of light emitted by the second light source, and there being provided electronic switching means for energizing the first and the second light source in alternation, and electronic control means responsive to the measured amount of reflected first light source light and reflected second light source light for so controlling the intensity of the second light source that the measured amounts of reflected light are substantially equal for each measuring region.

Experiments have shown that advantageously the light emitted by the first source is green and the light emitted by the second source is red. In fact, red and green light produce a maximum difference in amount of reflection from colorless and colored ribbon, respectively, for the coloring agent used, which enhances the accuracy of the measurement.

Although different known types of light sources may be used, the use of red and green light emitting diodes has proven extremely advantageous, especially on account of the high rate at which these light sources can be switched on and off. Photoresponsive resistors and silicon photodiodes may be used as light detecting means, with a preference for the latter as these photodiodes are instantly responsive to light variations, have little temperature dependence and exhibit a good linear relationship between illumination intensity and signal current.

The invention is based on the insight that it is possible to suppress the influence of the greyness of the ribbon by measuring the reflection of the ribbon at two suitable colors of light and by subsequently determining the ratio of the two reflection values measured. Also the influence of variations in mesh width of the ribbon is highly suppressed in this manner. Furthermore, the influence of the basic color of the ribbon can be eliminated by measuring the reflection of the ribbon at two different points, i.e. a first point located so close to the station where the ribbon is treated with the chemical liquid that no chemical reaction could possibly have taken place yet and a second point spaced from the first point by a distance corresponding to that travelled by the ribbon during a period of about 10 seconds being the period required for allowing the fact whether or not discoloration has taken place to be established with sufficient certainty. The quotient of the signals obtained at the two points of measurement then provides information only as to the discoloration of the ribbon during the 10 seconds period. It will be clear that this measuring procedure places a high demand on the constancy of the ratio between the intensities of the illumination with light of the same color at the two points of measurement. To meet this demand, in accordance with the invention there is provided an optical system delivering constant fractions of the light from the first and the second light source to the two measuring regions. In accordance with the invention, by so controlling the light from the second, red light source that the reflections measured at the first and the second measuring region, respectively, are equal for red light and green light, it is achieved that offset voltages and offset currents and non-linearities of the amplifiers in the electronic circuit as well as non-linearities of the photocells have no effect on the final result of the measurement.

Figure 2:
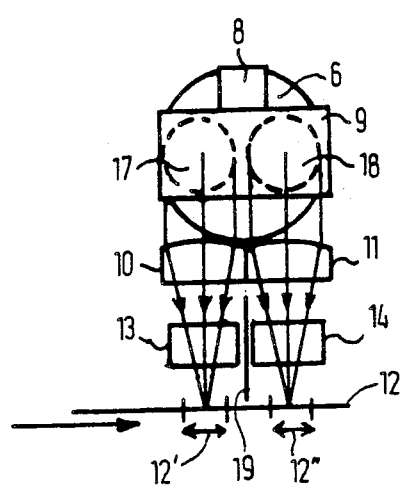
Figure 3:
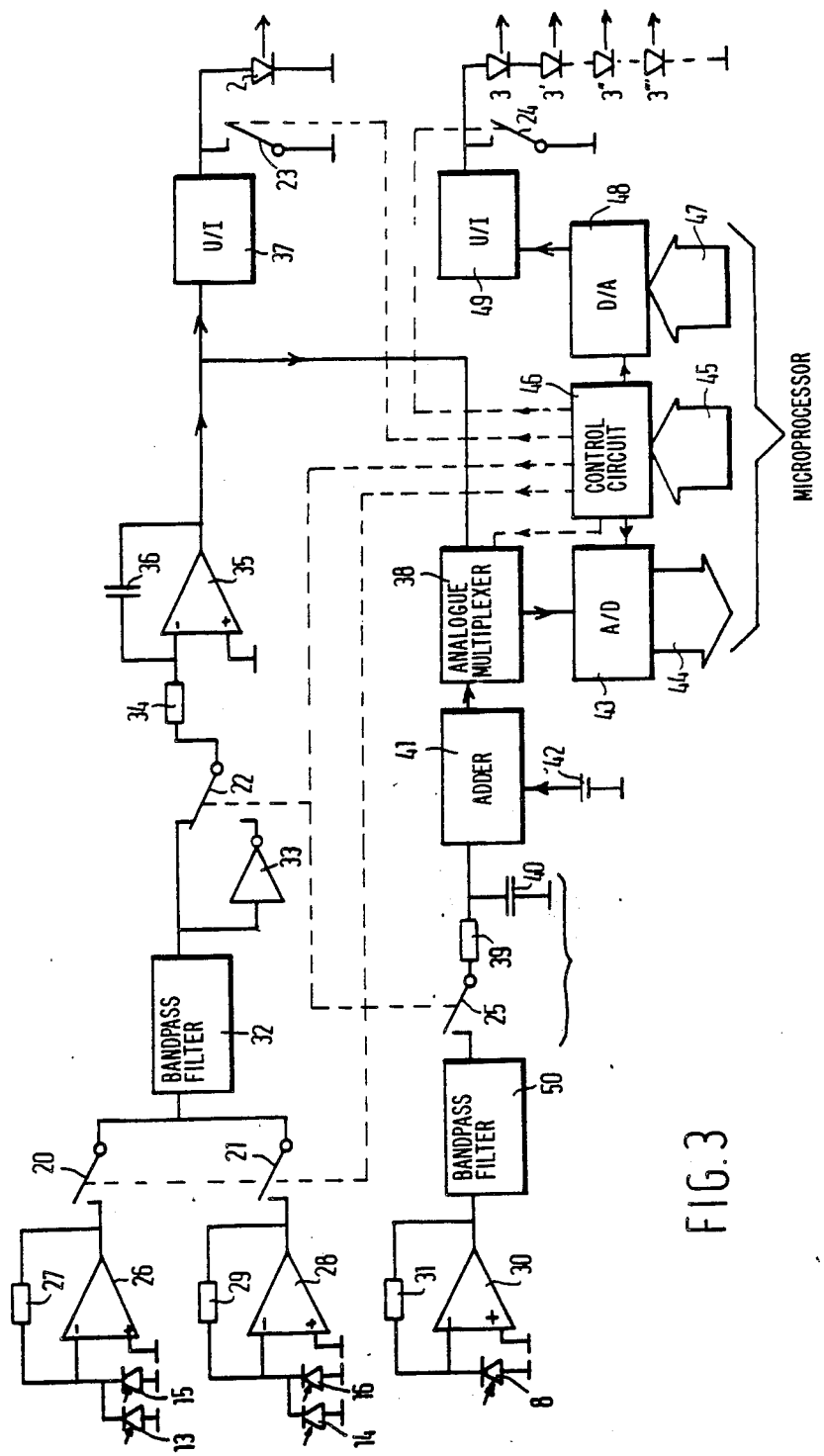
Figure 4:
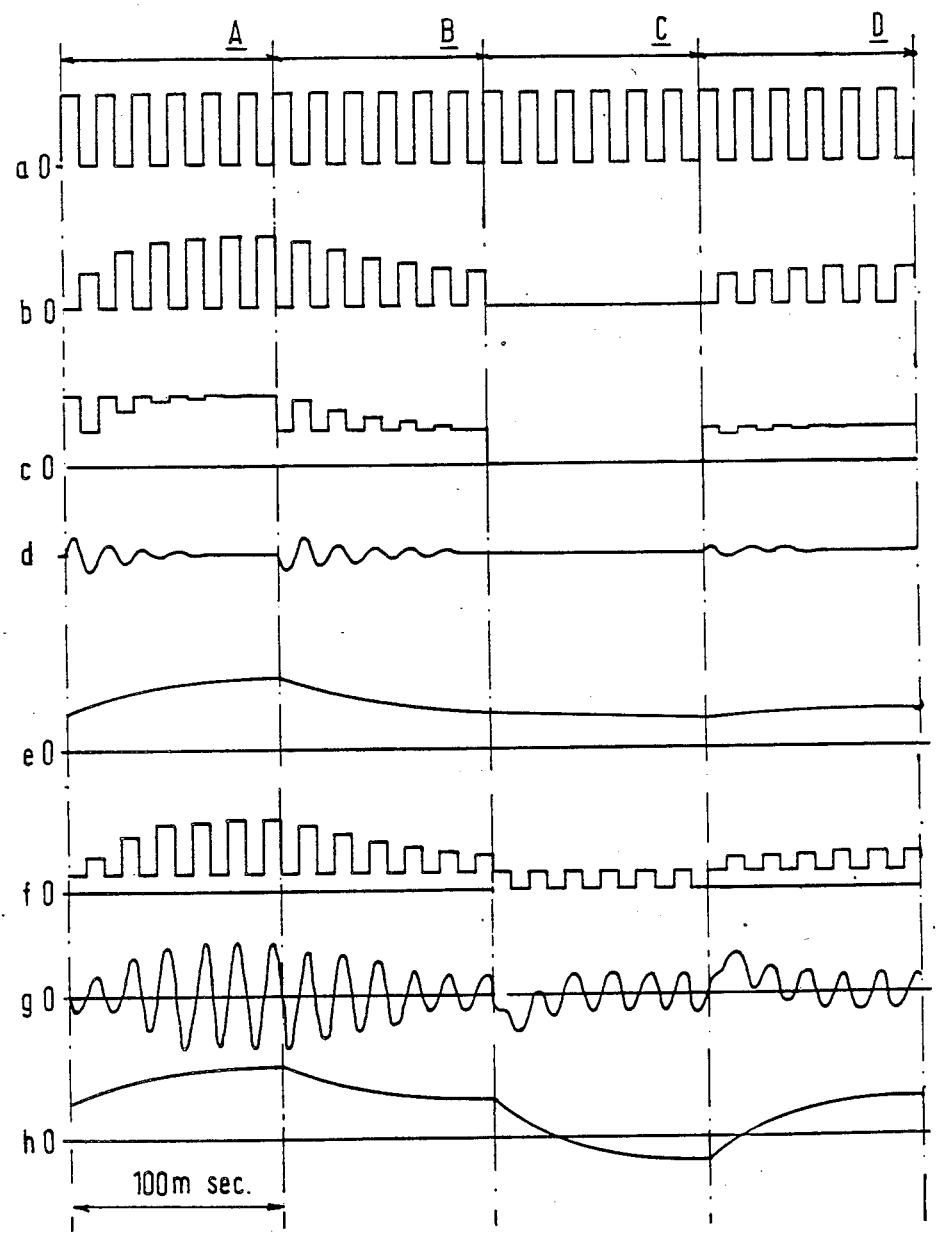

The invention will be described in greater detail hereinafter with reference to an embodiment thereof and in conjunction with the accompanying drawings, in which:

FIG. 1 schematically shows in side view the structure of the optical and illumination system of the detection device according to the invention;

FIG. 2 schematically shows in front view the structure of FIG. 1;

FIG. 3 schematically shows the electric circuitry for controlling the light sources in the illumination system and the means for detecting the reflected light; and FIG. 4 schematically shows a number of waveforms which can occur in the circuitry of FIG. 3.

FIGS. 1 and 2 show the illumination system 1 comprising a centrally mounted red LED 2 and preferably 4 to 6 green LEDs mounted in rotation-symmetrical fashion around LED 2, two of which being designated by reference numerals 3 and 3'. The reasons for using unequal numbers of LEDs are, firstly, that green LEDs emit light beams of lesser intensity than red LEDs and, secondly, that the silicon photocells used as light detecting means are less sensitive to green light than to red. A diffusor 4 mixes the light beams emitted by the different LEDs so that the beam emanating from it is optimally rotation-symmetrical with respect to the optical axis of the system. An optical system projects the aperture 5 of the illumination system 1 onto the ribbon 12 at two regions, which measuring regions are designated by reference numerals 12' and 12" in FIG. 2.

The optical system includes a main objective 6 converting the divergent light beam emanating from aperture 5 into a parallel light beam, and measuring field objectives 10 and 11 converging portions 17 and 18, respectively, of the total light beam emanating from objective 6 and reflected by a mirror 9 so that these portions are focussed on the ribbon. The symmetrical structure of both the illumination system and the optical system ensures that equal fractions of the light beam emanating from aperture 5 reach measuring region 12' and measuring region 12" on the ribbon.

A portion of the light beam emanating from objective 6 reaches a photocell 8 through a filter 7 passing only red light. The photocells 13 and 15 at measuring region 12' and 14 and 16 at measuring region 12" receive the light reflected by the ribbon. A nontransparent screen 19 prevents light reflected at one of the measuring regions from reaching the photocells associated with the other measuring region.

The optical system has essentially the same characteristics for red and green light. The red and green light spots on the ribbon coincide in so far as dimension and position are concerned, and the light intensity distribution within the measuring region is identical for both colors. This is an essential condition for a proper suppression of the variations in light reflection by the ribbon due to the varying ratio between thread thickness and mesh width within the measuring region, the so-called ribbon noise.

The spectrums of the red and green LEDs partially overlap and it is therefore not possible to construct an optical filter 7 blocking the total emission of the green LEDs and passing the total emission of the red LED. However, the electronic circuitry can be provided with facilities to be described later on for optimally eliminating the effect of green leakage light.

FIG. 3 shows a block diagram of the electronic circuitry for producing signals providing optimally accurate information on the color of the light at the two measuring regions. The LEDs and photocells shown in FIGS. 1 and 2 are designated by the same reference numerals in FIG. 3. The LEDs 3" and 3''' are shown to make it clear that the illumination system 1 can include four or more green LEDs and that, in principle, these LEDs are traversed by the same current.

The switches 20–25 in FIG. 3 are only schematically shown and will preferably be high-speed MOSFET switches in reality.

The silicon photocells 13 and 15 are connected in parallel relationship to the inverting input of an amplifier 26. The output of amplifier 26 is fed back through a resistor 27 to the inverting input in order to a low input impedance of this amplifier. This is desirable as silicon cells exhibit good linear characteristics and relatively little temperature dependence when operating with a low ohmic load.

The photocells 14 and 16 are similarly connected to an inverting input of a second amplifier 28 having its output likewise fed back through a resistor 29 to the inverting input. The photocell 8 is connected to the inverting input of an amplifier 30 having its output fed back through a resistor 31 to the inverting input. The non-inverting inputs of amplifiers 26, 28 and 30 are connected to ground.

The output signals from amplifiers 26 and 28 can be applied through switches 20 and 21, respectively, to the input of a bandpass filter 32. This bandpass filter 32 is operative to filter low frequency AC voltage components out of the output signals from amplifiers 26 and 28, which components are produced in response to daylight incident on the photocells and, during maintenance procedures, in response to artificial light. The output of amplifier 30 is connected to a bandpass filter 50 serving the same purpose as filter 32.

The output of bandpass filter 32 is connected to the input of a synchronous rectifier circuit comprising an inverter 33, a switch 22 and an integrator circuit composed of a resistor 34, an amplifier 35 and a feedback capacitor 36, resistor 34 being connected to the inverting input of amplifier 35 and capacitor 36 being connected between the output of amplifier 35 and its inverting input. The non-inverting input of amplifier 35 is connected to ground. The inverter 33 is operative to additionally suppress low frequency signals.

The output of amplifier 35 is connected to the input of a voltage-to-current converter 37 the output of which controls the red LED 2. The output of converter 37 can be connected to ground through a switch 23 so as to cut off the current to LED 2.

The output of bandpass filter 50 is connected to the input of a synchronous rectifier circuit composed of a switch 25, a resistor 39 and a capacitor 40. Capacitor 40 has its one terminal connected to ground and its other terminal connected to a terminal of resistor 39 and to the input of an adder circuit 41. Adder circuit 41 has a second input connected to a source 42 of DC voltage. The output of adder circuit 41 is connected to a first input of an analog multiplex circuit 38 having its second input connected to the output of amplifier 35. The output of circuit 38 is connected to an analog-to-digital converter 43 operative to convert the signal applied thereto into a data flow to be supplied through a data bus 44 to a microprocessor (not shown in FIG. 3). The microprocessor supplies through a data bus 45 control signals to a control circuit 46 operative to control the switches 22–25, the analog multiplier circuit 38, the analog-to-digital converter 43 and a digital-to-analog converter 48. Digital-to-analog converter 48 receives data from the microprocessor through a data bus 47. The output of digital-to-analog converter 48 is connected to a voltage-to-current converter 49 having its output connected to the series-connection of LEDs 3, 3', 3'', 3''' and any further green LEDs that may be present. The output of circuit 49 can be connected to ground through switch 24 in order to cut off the control of the LEDs.

The operation of the detection device according to the invention will now be described in greater detail.

As shown in FIGS. 1 and 2, there are two measuring regions 12' and 12'' on the ribbon, measuring region 12' being located close to the station where the ribbon is moistened with the chemicals causing discoloration and measuring region 12'' being located about 8 millimeters downstream in the direction of travel of the ribbon, which distance corresponds to a time interval of about 10 seconds at the selected speed of the ribbon, during which period the chemicals can cause discoloration of the ribbon when the atmosphere is clean or are prevented from causing such discoloration by the presence of the gases to be detected. At each measuring region the ribbon is alternately illuminated with green light of a wavelength of about 550 nanometers and red light of a wavelength of about 650 nanometers. The rate at which the illumination alternates in color is about 1 kHz, so that the distance travelled by the ribbon during a cycle of red and green light is negligible. Both measuring regions are illuminated from a single illumination system designated in FIG. 1 by reference numeral 1, which system is adapted to alternately emit red and green light. Each measuring region is associated with two silicon photocells, i.e. region 12' with photocells 13 and 15 and region 12'' with photocells 14 and 16, which receive part of the light reflected and dispersed by the ribbon and which, as shown in FIG. 3, are connected for use as a current source, whereby a rapid and linear response is ensured.

The intensity of the green light is constant in principle, while the intensity of the red light is so adjusted that at each measuring region the output signal of the parallel-connected photocells in response to red light is optimally equal to that in response to green light. Because of this control of the photocell signals, the absolute sensitivity and the dark current of the photocell, the offset currents and a possibly non-linear and non-constant current-brightness ratio of the red lamp do not affect the result of the measurement. The control system so controls switches 20 and 21 that the intensity of the red LED is controlled alternately for the two measuring regions during about 100 msec, so that at successive points of time an intensity for the red light is alternately adjusted which is a measure for the color of the ribbon at measuring region 12'and measuring region 12'' respectively. The quotient of these two intensity values, the color quotient Q, is a measure for the discoloration of the ribbon during the transport from measuring region 12' to measuring region 12''. In the calculations to be described hereinafter, $F_g$ = luminous intensity of the green light beam emanating from aperture 5

$F_r$ = luminous intensity of the red light beam emanating from aperture 5

$c_g$ = fraction of the green light beam incident on the ribbon at one measuring region $c_r$ = fraction of the red light beam incident on the ribbon at one measuring region $k_g$ = effective reflection coefficient of the ribbon for green light $k_r$ = effective reflection coefficient of the ribbon for red light $G_g$ = sensitivity to green light of the photocells associated with the ribbon (mA/Lm)

$G_r$ = sensitivity to red light of the photocells associated with the ribbon (mA/Lm).

If the control system has adjusted the intensity of the red light source in the manner described above, at each measuring region the following equation applies:

$$F_g \cdot c_g \cdot k_g \cdot G_g = F_r \cdot c_r \cdot k_r \cdot G_r,$$

so that:

$$F_r = F_g \cdot \frac{c_g}{c_r} \cdot \frac{k_g}{k_r} \cdot \frac{G_g}{G_r} \quad (1)$$

As $c_g/c_r$ and $G_g/G_r$ are essentially constant, $F_r$ is adjusted at a value which is directly proportional to $F_g$ and further depends on the color of the ribbon.

It is assumed that, using the photocell currents at measuring region 12' as the criterion, the control system adjusts the intensity of the red light beam at the value Fr1 and subsequently, using the photocell currents at measuring region 12" as the criterion, at the value Fr2.

The following equation then applies to the ratio Fr1:Fr2, i.e. the color quotient Q of the ribbon at the two measuring regions:

$$Q = \frac{Fr1}{Fr2} = \frac{Fg1}{Fg2} \cdot \frac{cg1}{cg2} \cdot \frac{cr2}{cg2} \cdot \frac{kg1}{kr1} \cdot \frac{kr2}{kg2} \cdot \frac{Gg1}{Gr1} \cdot \frac{Gr2}{Gg2} \quad (2)$$

Equation (2) can be simplified as:
1. Fg1=Fg2, as there is one constant, green light source common to both measuring regions;
2. The various c-values are equal in principle and are any rate constant; and
3. The quotients $$\frac{Gg1}{Gr1} \text{ and } \frac{Gg2}{Gr2}$$

are approximately equal (the same type of photocell) and are at any rate constant.
As a result, equation (2) is simplified into:

$$Q = \frac{Fr1}{Fr2} = K \cdot \frac{kg1}{kr1} \cdot \frac{kr2}{kg2} \quad (3)$$

In equation (3), $K \approx 1$ and is at any rate of constant magnitude.

By determining the color quotient Q in the above manner, it is achieved that this color quotient is not affected by variations in thread thickness and mesh width of the ribbon, as in principle these factors equally affect kg and kr at each measuring region, and that in principle variations in the basic color of the ribbon or in the basic color of the chemicals equally affect kg1 and kg2, and kr1 and kr2 at the respective measuring regions.

The colors red and green are used for illuminating the ribbon as the color formed on the ribbon when the atmosphere is clean results in a relatively large reduction of the reflection of the ribbon for green light and a relatively small reduction of the reflection for red light. The color quotient Q is approximately 1.1 for colored ribbon and approximately 1 for uncolored ribbon. As a result, a relatively large output signal is provided, which reduces the liability of measuring errors.

The luminous intensities Fr1 and Fr2 are measured by photocell 8. This photocell receives from objective 6 a constant portion of the light beam emanating from aperture 5. As only the red light needs to be measured by means of photocell 8 and not the green light present in the beam, a filter 7 passing red light and blocking green light is mounted in front of photocell 8.

Photocell 8 alternately produces the following signals:

S1=cr3.Gr3.Fr1+d and S2=cr3.Gr3.Fr2+d, where:
cr3=portion of the red light beam incident on photocell 8;
Gr3=sensitivity to red light of photocell 8; and
d=dark and offset current.

As for an accurate determination of Q the signal quotient S1/S2 should be optimally equal to the light quotient Fr1/Fr2, S1 and S2 have to be corrected for the value of d. To this end, the measuring cycle during which Fr1 and Fr2 are alternately so controlled that they are equal to Fg1 and Fg2, respectively, also includes a measuring phase for the dark current, during which phase the red light source is switched off and hence Fr=0. Photocell 8 and the amplifier circuit connected between this photocell and analog-to-digital converter 43 than together produce signal component d. The signals from photocell 8 are digitally processed via analog-to-digital converter 43 and the microprocessor. Signals S1, S2 and d are successively converted into digital form and stored in the memory of the microprocessor. The pure color quotient Q can be computed from these data in the following manner:

$$Q = \frac{S1 - d}{S2 - d}.$$

It will be clear from the above that the system described is highly irresponsive to the absolute values and the slow variations of the ratio between the luminous intensity and the supply current of the red and green LEDs; the sensitivity and the dark current of the photocells; the offset voltages and offset currents of all amplifiers in the circuitry; the basic color of the ribbon and of the chemical moistening agents; and variations in thread thickness and mesh width of the piece of ribbon located in the field of measurement, the so-called ribbon noise.

The operation of the electrical circuitry shown in FIG. 3 will be further elucidated hereinafter with reference to FIG. 4 showing a number of waveforms occurring in this circuitry.

The control cycle comprises the following four measuring intervals of about 100 milliseconds each, designated in FIG. 4 by A, B, C and D respectively.

Interval A:
The red light is controlled using the signal produced by photocells 13 and 15 associated with measuring region 12' as the criterion. Switch 20 is closed and switch 21 is open, while switches 23 and 24 are so energized and deenergized in a 1 kHz rythm that when switch 23 is open, switch 24 is closed and vice versa. As a result, the red and green LEDs are alternately energized. FIG. 4a shows the emission of the green LEDs and FIG. 4b the emission of the red LED.

Interval B:
The red light is controlled using the signal produced by photocells 14 and 16 associated with measuring region 12" as the criterion; switch 20 is open and switch 21 is closed, while switches 23 and 24 continue to be energized and deenergized in a 1 kHz rythm.

Interval C:
The dark and offset currents are measured; switches 20 and 21 are both open and switch 23 is closed, so that no red light is emitted by LED 2, while switch 24 continues to be energized and deenergized in a 1 kHz rythm, so that the green LEDs emit their usual amount of green light.

Interval D:
The red light is controlled using the signal produced by photocells 14 and 16 associated with measuring region 12" as the criterion; switch 20 is open, switch 21 is closed and switches 23 and 24 are energized and deenergized in a 1 kHz rythm.

The control cycle is repeated after interval D.
At the end of each interval the signal from photocell 8 is converted into digital form and applied to the microprocessor. During each control cycle two measurements pertaining to measuring region 12" and one measurement pertaining to measuring region 12' are obtained. The reason for this is that changes, if any, occurring at measuring region 12' may be expected to only be gradual ones, while the presence or absence of discoloration will be exhibited at measuring region 12" and has to be established with as small a loss of time as possible. Variations in the dark and offset currents will likewise be gradual ones, so that one measurement of these currents per control cycle suffices.

At the beginning of a control interval, the ratio between the red and the green light detected by the photocells associated with the ribbon will differ from 1, so that bandpass filter 32 receives at its input a signal as shown in FIG. 4c and produces at its output a signal as shown in FIG. 4d. By synchronous rectification via switch 22, which is likewise energized and deenergized in a 1 kHz rhythm, a direct current is obtained the polarity and magnitude of which depend upon the absolute difference between the amplitudes of the signals produced by the photocells in response to the light from the red LED and the green LEDs, respectively. The rectified current is integrated by the integrator. The output voltage of the integrator, i.e. the output voltage of amplifier 35, is shown in FIG. 4e. As long as the photocells associated with the ribbon detect an excess of green light over red, the output voltage of the integrator will increase whereas this output voltage will decrease as long as the photocells detect an excess of red light over green. When photocells 13, 15 and 14, 16, respectively, produce as much signal current in response to green light as in response to red light, no 1 kHz AC voltage is applied to bandpass filter 32 any longer, so that the input current of the integrator is zero and the output signal of the integrator remains constant.

By a suitable choice of the total loop gain and the time constant defined by resistor 34 and capacitor 36, the equilibrium state within the interval of 100 milliseconds is reached, as appears clearly from especially FIGS. 4d and 4e.

Photocell 8 directly receives light from the red LED 2 and a portion of the green light from LEDs 3, 3' etc. in so far as this green light is passed by filter 7. The signal from photodiode 8 is shown in FIG. 4f. Bandpass filter 50 produces an AC output voltage shown in FIG. 4g the peak-to-peak value of which is proportional to the difference between the output current of photocell 8 in response to red light and that in response to green leakage light. During the dark current compensation interval C, the red LED is off. Bandpass filter 50 then produces an output voltage the peak-to-peak value of which is proportional to the current of photocell 8 in response to green leakage light. In the presence of only green leakage light, the phase of the output signal of bandpass filter 50 is shifted 180° relative to that of the signal produced in response to both red light and green leakage light. These phase jumps are shown in FIGS. 4f and 4g both at the transition from interval B to interval C and at that from interval C to interval D.

In adder circuit 41 the signal from the synchronous rectifier circuit composed of switch 25, resistor 39 and capacitor 40 is shifted in DC voltage in order to bring the output voltage of the adder circuit within the input voltage range of analog-to-digital converter 43. To this end, the second input of adder circuit 41 is coupled to DC voltage source 42. The signal present on the first input of circuit 41 is shown in FIG. 4h.

The signal transmission from photocell 8 to the output of adder circuit 41 takes place as follows.

Photocell 8 produces a current ir in response to red light and a current ig in response to green light. Bandpass filter 50 blocks the mean component (ir+ig):2 and amplifies the AC voltage component ir−ig to a signal voltage U1 having a peak-to-peak value U1=G.(ir−ig). The synchronous rectifier supplies a positive DC voltage U2=½G.(ir−ig) to the adder circuit. It is assumed in this connection that switch 25 is closed during the positive half cycle of the AC voltage signal U1. Adder circuit 41 adds a fixed DC voltage U0 to U2, resulting in an output voltage Us=½G.(ir−ig)+UO. This signal is applied to analog multiplex circuit 38, converted into digital form and stored in the microprocessor.

During measuring interval C there applies ir=0, so that during this interval adder circuit 41 produces an output signal Ud=½G.(−ig)+UO. This signal is likewise converted into digital form and stored in the microprocessor.

Subtraction of Us and Ud results in: Us−Ud=½G.(ir−ig)+UO−½G.(−ig)−UO=½G.ir.

In each one of the three control periods of a control cycle an ir-value is adjusted; the ig-value is constant in principle as the current traversing the green LEDs is set at a fixed value.

The control at measuring region 12' results in the signal Us1−Ud=½G.ir1, while the control at measuring region 12", which takes place twice per measuring cycle, results in the signal Us2−Ud=½G.ir2.

The color quotient Q can now be calculated from $$Q = \frac{Us1 - Ud}{Us2 - Ud} = \frac{ir1}{ir2}.$$

A ribbon section located at measuring region 12' at a given point of time will pass measuring region 12" after about 10 seconds. By taking the most recent ir2-value and the ir1-value of 10 seconds earlier when determining the color quotient $$Q = \frac{ir1}{ir2},$$

a Q-value is obtained that relates to the same ribbon section and hence is optimally indicative of the discoloration experienced by a given ribbon section during the displacement from measuring region 12' to measuring region 12".

In spite of the steps taken in the optical system for the purpose of equalizing the ratio between red and green light for all parts of the ribbon within the measuring region, nevertheless ribbon noise will occur as not all portions of the moistened threads of the ribbon and the meshes of the ribbon filled with varying amounts of moistening liquid will reflect the red and green light with the same intensity and in the same direction. Consequently, successive values of ir will exhibit small differences. To eliminate this noise effect, when determining the quotient an ir1-value may be used that is the average of five measurements, the middle one of which is that performed nominally 10 seconds earlier.

The microprocessor system produces an alarm signal in response to the color quotient Q exceeding a predetermined threshold value. This threshold value can be a temperature-dependent value as at relatively high temperatures more coloring matter is formed on the ribbon after 10 seconds than at relatively low temperatures.

The output signal of the integrator circuit composed of resistor 34, amplifier 35 and capacitor 36 is applied to the analog multiplex circuit 38 and analog-to-digital converter 43 for the purpose of error detection. When due to a faulty component or outside influences, for example fouling of a photocell, the control circuitry fails to operate properly, in most cases the output voltage of the integrator will no longer be within the normal dynamic operating range, which phenomenon can be used for causing the microprocessor to produce an error signal.

Although the device for detecting differences in color in accordance with the invention has been described by way of example with reference to its use in a gas detector, self-evidently other uses of the device are not excluded.

I claim:

1. A device for detecting differences in color of a material to be inspected, which comprises:
    means for illuminating said material including a first light source emitting light of a first color and a second light source emitting light of a second color;
    means for measuring amounts of light reflected by said material;
    electronic switching means for alternately energizing at a first rate said first and second light source;
    electronic control means responsive to said measured amounts of reflected first light source light and reflected second light source light for controlling intensity of said second light aource whereby measured amounts of reflected first and second light source lights, respectively, have a predetermined ratio;
    means for providing second light source signals representing amount of light emitted by said second light source during a measurement;
    an optical system for delivering to first and second spaced-apart measuring regions simultaneously a constant portion of said light source being energized, said reflected light measuring means making a first measurement at said first measuring region and subsequently making a second measurement at said second measuring region, said second light source signals providing means comprising means for providing said second light source signals during said first and said second measurements, respectively; and
    means to detect a difference between said second light source signals during said first and said second measurements, respectively.

2. The device as defined by claim 1 and further including means for transporting said material from said first measuring region to said second measuring region and means to delay said second light source signal obtained during said first measurement for a time approximately equal to time necessary to transport said material from said first measuring region to said second measuring region.

3. The device as defined by claim 2 and further including alternating means for controlling said reflected light measurement means to make said first and said second measurements continuously at a second rate, said second rate being lower than said first rate.

4. The device as defined in claim 3 wherein said reflected light measuring means comprise at least one light detector at each measuring region and wherein said alternating means are second electronic switching means.

5. The device as defined by claims 1 or 2 wherein said first switching means energizes said first light source only during a predetermined period of time, an output signal of said means for providing said second light source signal being a measure for an offset current and dark current and wherein said value of said output signal is stored.

6. The device as defined by claims 1 or 2 wherein said detecting means determines a ratio between said second light source signals and wherein a signal representative of said ratio and a signal with a predetermined value are compared and an alarm signal generated in response to said signal of predetermined value being exceeded by said signal representative of said ratio.

7. The device as defined by claims 1 or 2 wherein constant portions of said light emitted by said light sources being energized are equal.

8. The device as defined by claims 1 or 2 wherein said light sources are light emitting diodes, a color of said first light source being green and a color of said second light source being red, said measuring means including at least one silicon photodiode at each measuring region and wherein said means providing said second light source signals includes a silicon photodiode provided with a filter operative to optimally block green light.

9. The device as defined by claims 1 or 2 and further including a diffusor mounted in front of said light sources, said light sources and diffusor being mounted in a housing having an aperture, an objective for converting divergent light beam emanating from said aperture into a parallel light beam, a portion of said parallel light reaching said means for providing said second light source signals, and an additional optical means through which another portion of said parallel light beam passes to both of said measuring regions.

* * * * *